(12) United States Patent
Graham

(10) Patent No.: US 6,790,036 B2
(45) Date of Patent: Sep. 14, 2004

(54) ORTHODONTIC TOOTH REPOSITIONER (76) Inventor: Neil John Graham, 6017 Lido La., Long Beach, CA (US) 90803

( * ) Notice: Subject to any disclaimer, the term of this patent is extended or adjusted under 35 U.S.C. 154(b) by 246 days.

(21) Appl. No.: 10/152,442

(22) Filed: May 23, 2002

(65) Prior Publication Data
US 2003/0219690 A1 Nov. 27, 2003

(51) Int. Cl.$^7$ .................................................. A61C 3/00
(52) U.S. Cl. .......................................... 433/6; 128/859
(58) Field of Search ....................... 433/6, 24; 128/859, 128/861, 862

(56) References Cited

U.S. PATENT DOCUMENTS

| | | | | |
|---|---|---|---|---|
| 4,784,605 A | * | 11/1988 | Bergersen | 433/6 |
| 4,798,534 A | * | 1/1989 | Breads | 433/6 |
| 4,799,884 A | * | 1/1989 | Bergersen | 433/6 |
| 5,055,039 A | * | 10/1991 | Abbatte et al. | 433/24 |
| 5,203,695 A | * | 4/1993 | Bergersen | 433/6 |
| 5,692,894 A | * | 12/1997 | Schwartz et al. | 433/6 |
| 5,876,199 A | * | 3/1999 | Bergersen | 433/6 |
| 5,975,893 A | * | 11/1999 | Chishti et al. | 433/6 |
| 6,293,790 B1 | * | 9/2001 | Hilliard | 433/4 |
| 6,454,565 B2 | * | 9/2002 | Phan et al. | 433/6 |

OTHER PUBLICATIONS

Essix Co.website http://www. essix.com May 2002.
Invisalign Co. website http://www.aligntech.com May 2002.

* cited by examiner

Primary Examiner—Ralph A. Lewis
(74) Attorney, Agent, or Firm—Neil John Graham

(57) ABSTRACT

A removable orthodontic appliance used to align the teeth of patient. The appliance is constructed to represent the patient's teeth in an aligned position. The material the appliance is constructed of is characterized by flexibility allowing a single appliance to move the patient's teeth into an aligned position. A single tooth may be moved with the appliance, but most commonly the appliance works best when teeth are mutually moved, most effectively, the six anterior teeth. The appliance may contain wires to widen or narrow the posterior width of the appliance and it also may contain a habit shield for tongue thrusting.

10 Claims, 8 Drawing Sheets

ORTHODONTIC TOOTH REPOSITIONER

FIELD OF THE INVENTION

The present invention relates to a removable orthodontic appliance for aligning teeth, and more particularly, to an appliance that is individually constructed for each dental arch with teeth in their aligned positions. The appliance material possesses a combination of firmness and flexibility wherein a single appliance, with minor adjustments, will move the teeth to their final aligned positions.

BACKGROUND OF THE INVENTION

Removable orthodontic appliances have been used in orthodontics since the early part of the 20th century. To clarify the description of the invention certain dental terms should be understood. Upper and lower teeth are termed maxillary and mandibular teeth, respectively. Front teeth are anterior teeth and back teeth are posterior teeth. Anterior teeth are incisors and are named centrals, laterals, and cuspids in order from the midline to the posterior. The posterior teeth, from anterior to posterior, are first, second, and third molars. Individual teeth are described according to their surfaces. The distal surface is towards the back of the mouth and the mesial is the surface towards the front of the mouth. The lingual or palatal surface is on the tongue side of the teeth. The labial or buccal surface is on the cheek or lip side of the teeth. The occlusal surface is where the maxillary and mandibular teeth meet.

Prior appliances required, many times, complicated adjustments and were not predictably effective in aligning crooked teeth. Another group of appliances were developed wherein the appliance is fabricated over a model of repositioned teeth. In this group is a tooth positioner, as disclosed in U.S. Pat. No. 2,531,222. The tooth positioner is one piece, moving the upper and lower teeth simultaneously. This appliance is very demanding on patients as they are bulky, uncomfortable, and prevent patients from speaking. Also in this group, are appliances known as spring-alignment appliances. These appliances are designed to correct minor incisor rotations. The appliance is constructed over a model of repositioned teeth. Labial and lingual wires are formed and labial and lingual plates are formed over the wires. The acrylic plates apply the pressure to the teeth. These appliances cannot be adjusted and are not particularly effective for tooth movement. Another in this group, is the INVISILIGN appliance, which is made by vacuum forming a clear maternal over many models of progressively positioned teeth. The INVISILIGN appliance uses a relatively hard material which prevents an individual appliance from producing substantial tooth movement. For this reason, a series of appliances have been constructed where the movement is progressive, each succeeding appliance applies slightly more movement than the prior appliance INVISILIGN claims average treatment is 9–15 months and each pair of all liners is worn two weeks. The number of appliances used would be from 36 to 60. The INVISILIGN appliances are very costly and their construction is difficult and very proprietary as the progressive tooth movement is computer generated by only the INVISILIGN company. The orthodontic profession to the present has an unfilled need for an effective, aesthetic, easy to construct, and cost-efficient removable appliance for aligning teeth.

SUMMARY OF INVENTION

An object of the present invention is to provide an esthetic, easy to wear, effective, removable orthodontic appliance. The removable appliance has its greatest usefulness when the posterior teeth are well positioned and the anterior teeth are misaligned, maloccluded, or otherwise in need of repositioning. The posterior teeth are the anchor for the appliance.

A preferred embodiment of the present invention comprises a sheet of 0.030 in. clear polypropylene thermo-vacuum formed to a model of the patient's teeth where the misaligned six anterior teeth are repositioned into an aligned position. The tooth movement being most effective where all six anterior teeth are repositioned. The concept of moving at least six anterior teeth is one of the keys of the success of this appliance. The embodiment is characterized by material that has a flexibility which allows a single retainer to move the misaligned teeth and into their final positions. Other materials, ranging from 0.020 inch thickness to 0.080 inch thickness may be used if they possess comparable flexibility to move the teeth. The appliances are made separately for each jaw, allowing the patient to wear appliances near full-time, if necessary. The appliance may also be constructed to move posterior teeth. An additional object of this invention is to ease the construction of the appliance. A single tooth repositioned model is usually all that is required, making construction of the appliance easy and economic. The single appliance ability of this appliance to align the teeth is further enhanced by stretching and cutting adjustments to allow the appliance to be seated in the mouth and retightening adjustments enabling the single appliance to move the teeth to a final aligned position.

In another embodiment of the present invention, the appliance is constructed with an embedded wire 0.020 inch to 0.060 inch in diameter to widen or narrow the posterior arch width. This is particularly effective for correction of posterior cross bites. The embedded wire has a further advantage of increasing stability and retention of the appliance. In a further embodiment of the appliance, a lingual shield is formed to prevent the adverse effect of the tongue upon the teeth, or as is commonly called, tongue thrusting. The shield is usually placed lingual to the anterior teeth, but may be used lingual to the posterior teeth for lateral tongue-thrusting patients. The shield is comfortable to wear and easy to construct. The template shield is affixed to the model in the lingual vertical position and the appliance is formed over the model, including the shield template. Other objects, features, and advantages of the invention will be apparent from the accompanying sheets of drawings wherein like reference numerals refer to like parts.

DETAILED DESCRIPTION OF THE INVENTION

Figure 1:
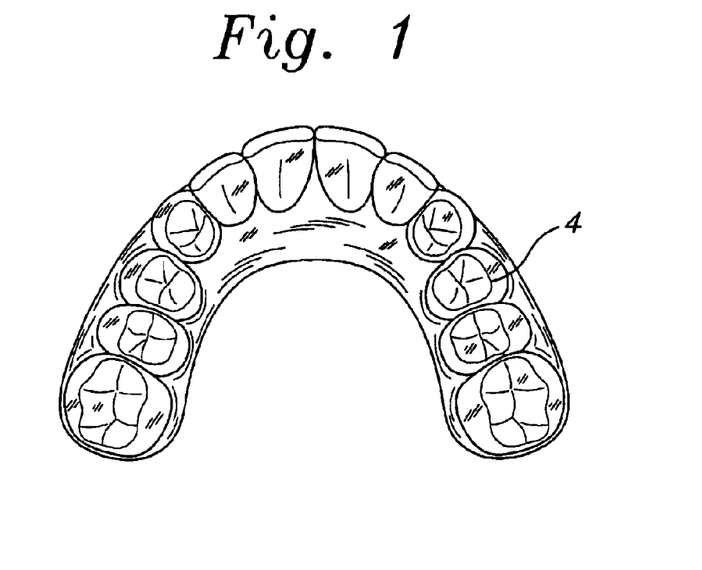
FIG. 1 is an occlusal view of the maxillary tooth repositioner.
Figure 2:
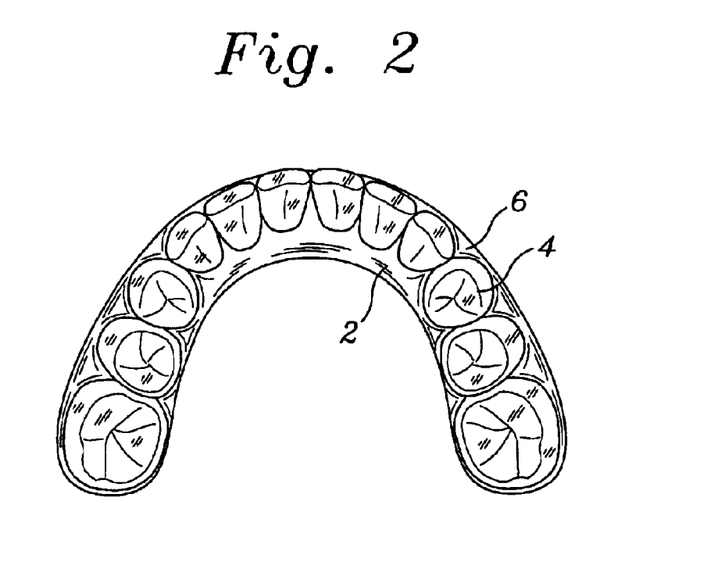
FIG. 2 is an occlusal view of the mandibular tooth repositioner.
Figure 3:
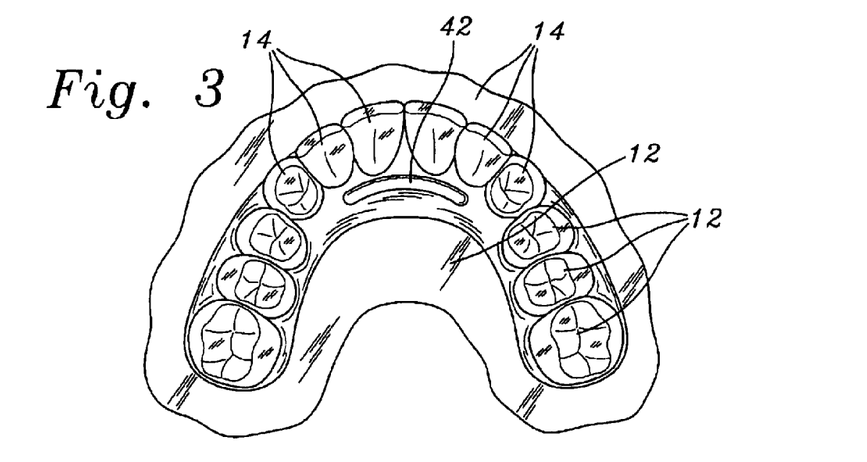
FIG. 3 is an occlusal view of the tooth repositioner on a model of a patient's teeth.
Figure 4:
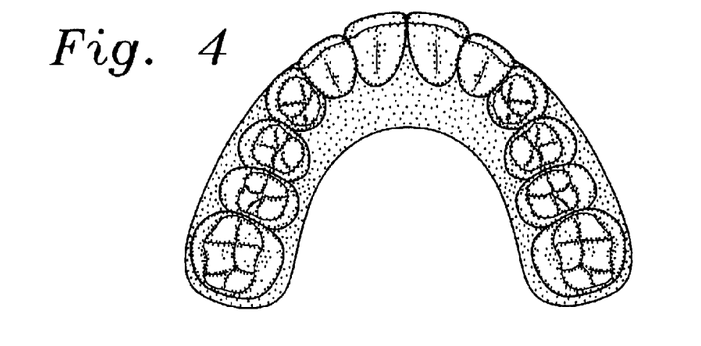
FIG. 4 is an occlusal diagramatic view of a patiet's teeth.

Referring to FIGS. 1–3, the tooth repositioner appliance is a single sheet of material formed over a patient's teeth 4 and adjacent soft tissue 2 and 6. The appliance FIGS. 1 and 2 can be formed from a variety of materials, such as polymers and plastics that possess the characteristics as described below. These materials can range in thickness from 0.020 in. to 0.080 inch, depending upon the material's physical characteristics.

A preferred embodiment of the appliance is 0.030 inch thick polypropylene which has been thermo vacuum-formed over a model 12 of a patient's teeth FIG. 3. The polypropylene is tissue compatible and clear which makes it aesthetically appealing to the patient during its use. The appliance has its best use when only the anterior teeth 14 require aligning and the posterior teeth 12, requiring no alignment, become an anchor for the appliance. The appliance can be used to align posterior teeth 12 individually or to widen or narrow the dental arch width, as discussed below.

Figure 5:
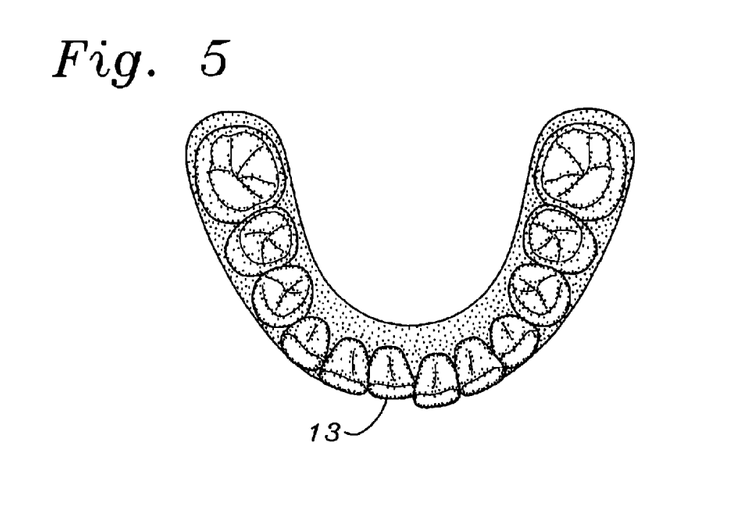
FIG. 5 is an occlusal diagramatic view of a patient's teeth with misaligned anterior teeth.
Figure 7:
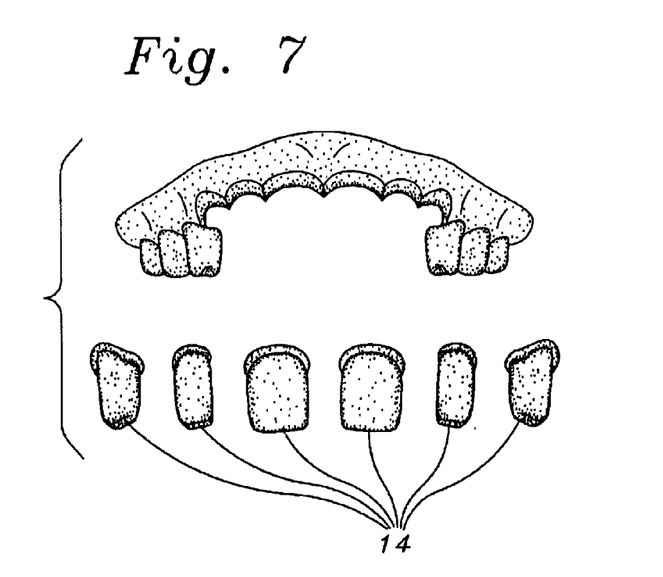
FIG. 7 is an occlusal view of a model of a patient's teeth where the anterior teeth have been removed.
Figure 8:
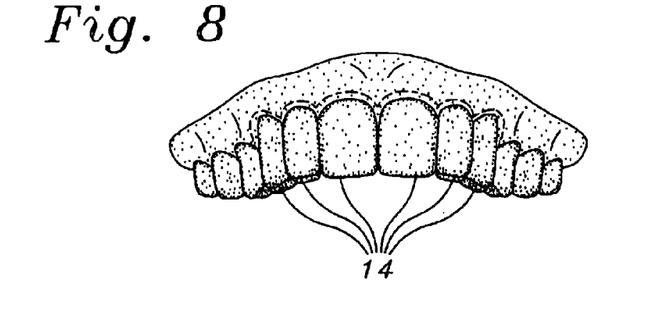
FIG. 8 is an occlusal view of the model shown in FIG. 7 wherein the anterior teeth have been repositioned in an aligned position.
Figure 9:
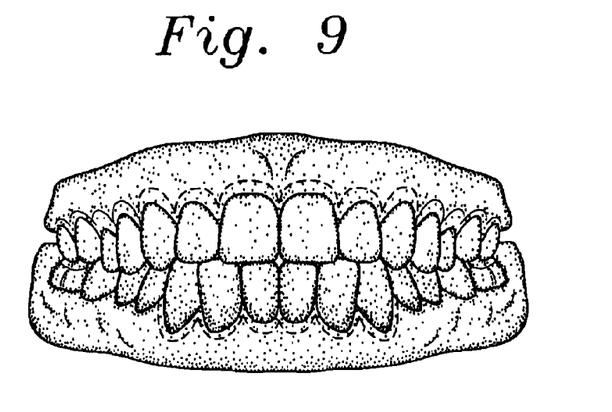
FIG. 9 is an anterior view of maxillary and mandibular repositioned models of teeth fitted in occlusion.

An important concept in aligning anterior teeth 14 is, when a single tooth only appears to be out of line, all six anterior teeth are moved. This approach has made the appliance the most effective. The tooth repositioner is constructed by using a mold of the patients teeth in their misaligned position's FIG. 5, individually removing the six anterior teeth FIG. 7, replacing the teeth in an aligned position FIG. 8, and thermo vacuum-forming the 0.030 inch polypropylene over the tooth aligned model. Aligning of teeth may also be accomplished using a computer-generated stereolithography model. The alignment of the anterior teeth is best done when the positions of the realigned teeth are repositioned to fit the patient's opposing teeth. FIG. 9 demonstrates the teeth aligned in both upper and lower jaws with the occlusion coordinated.

Figure 6:
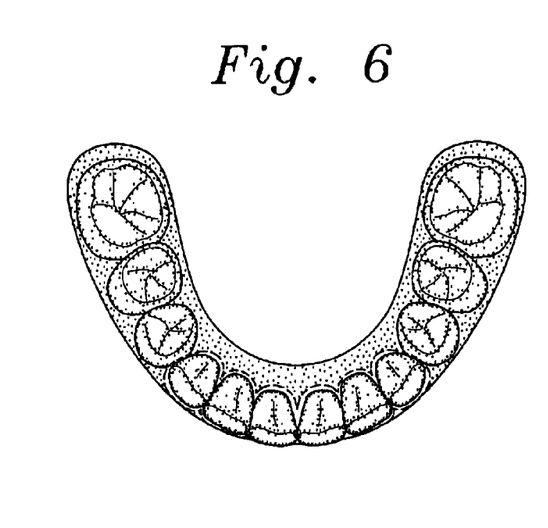
FIG. 6 is an occusal diagramatic view of a patient's teeth of FIG. 5 where the anterior teeth have been aligned.
Figure 10:
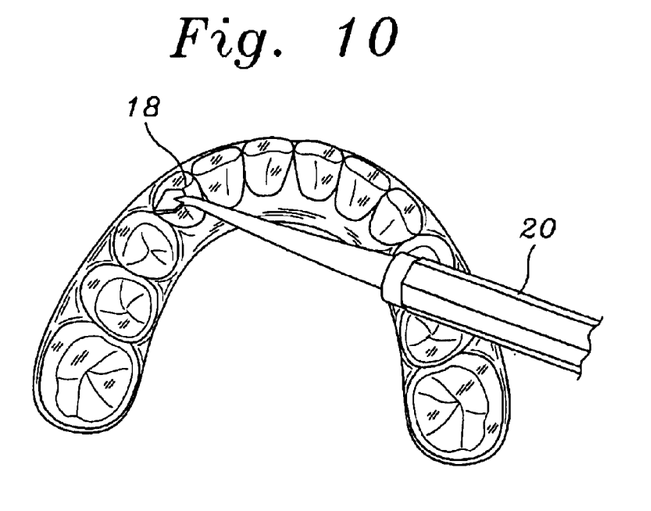
FIG. 10 is an occlusal view of a repositioner appliance being stretched with an instrument.
Figure 11:
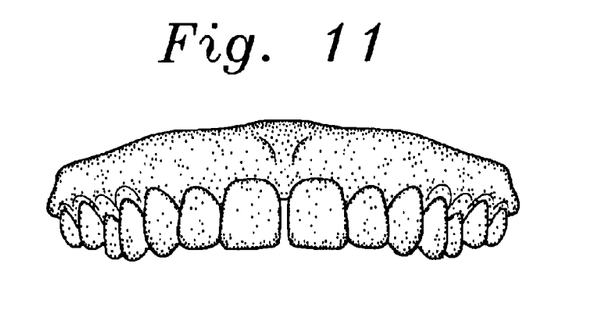
FIG. 11 is an anterior view of a model of a patient's teeth with a space between the central incisors.
Figure 12:
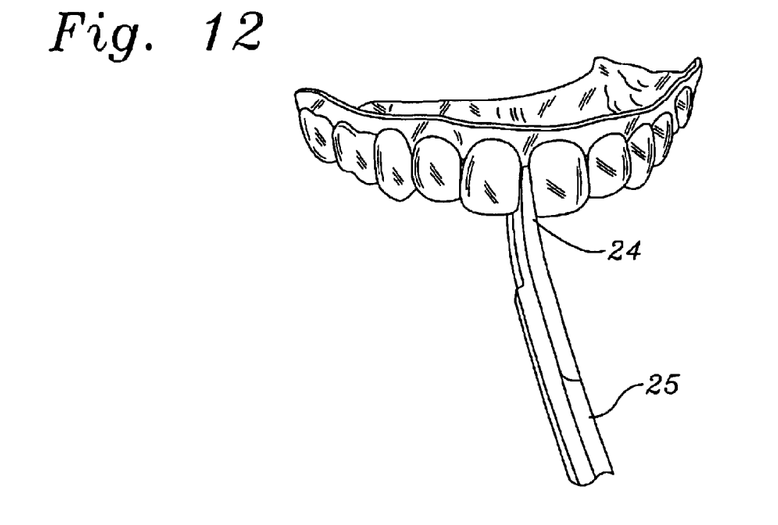
FIG. 12 is an anterior view of a repositioner appliance cut between the central incisors.

The 0.030 inch polypropylene is firm enough to move the patient's teeth and is flexible enough to adapt to the patient's misaligned teeth. These characteristics are essential for the purpose of this invention, that purpose being a single appliance can move the patient's teeth from misalignment FIG. 5 to alignment FIG. 6. A blunt instrument 20 is used to stretch the appliance material 18, FIG. 10, in areas where the teeth offer the most resistance to seating the appliance in the patient's mouth. The areas requiring stretching usually are the most misaligned teeth. Another technique of adapting the appliance to the patient's misaligned teeth is where an appliance is constructed in order to close the space for a diastema, or spaces between the patient's teeth FIG. 11. The appliance FIG. 12 is cut 24 with scissors between the central incisor teeth from the incisal or occlusal edge to the gingival area of the teeth. The cutting creates a loosening of the appliance allowing it to be seated and producing a tolerable force to the patient. The loosening adjustments of FIG. 10 are followed by the tightening adjustments of FIG. 13 using the blunt instrument 20 to re-form the material to its original shape which increases the force upon the patient's teeth. In the case of the cut appliance, the cut area can be re-seamed by holding the cut area FIG. 11 together and applying an instrument heated sufficiently to melt the polypropylene.

Figure 14:
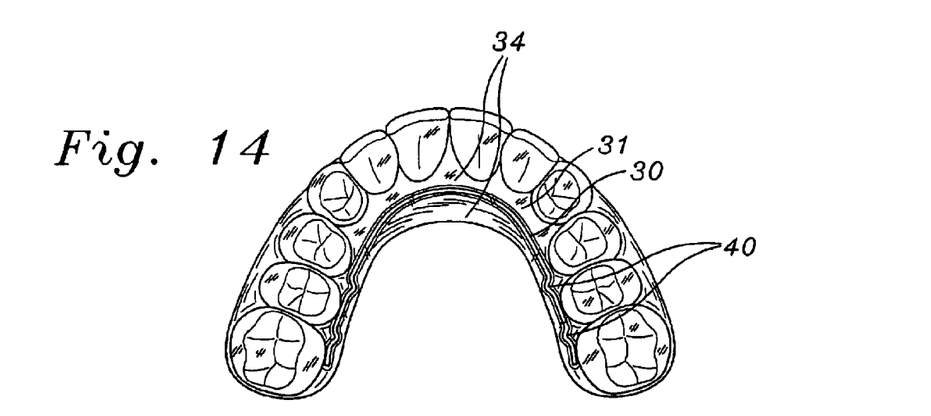
FIG. 14 is an occlusal view of another embodient of the repositioner appliance with an embedded wire in the palatal area.

Another embodiment of the appliance FIG. 14 is the placing a wire 30 in the palatal area of the appliance FIG. 14 which allows appliance to be adjusted to widen or narrow the patient's dental arch width. The wire can be 0.020 inch to 0.080 inch in diameter, 0.045 inch stainless-steel wire being preferred. The wire is arcuate 30 in form extending in palatal 30 portion of the appliance 31 from the molar area to the palatal area of the incisors FIG. 14 and to the molar area on the opposite side.

The wire 30 is embedded within the plate material, except in the incisal area where it is left open to the tissue side of the appliance. The wire 30 in this open area 34 is adjusted by increasing the arc of the wire which narrows the posterior of the appliance, or by decreasing the arc which widens the posterior of the appliance. This adjustment is most efficiently performed with an orthodontic instrument called a three-prong plier.

Figure 13:
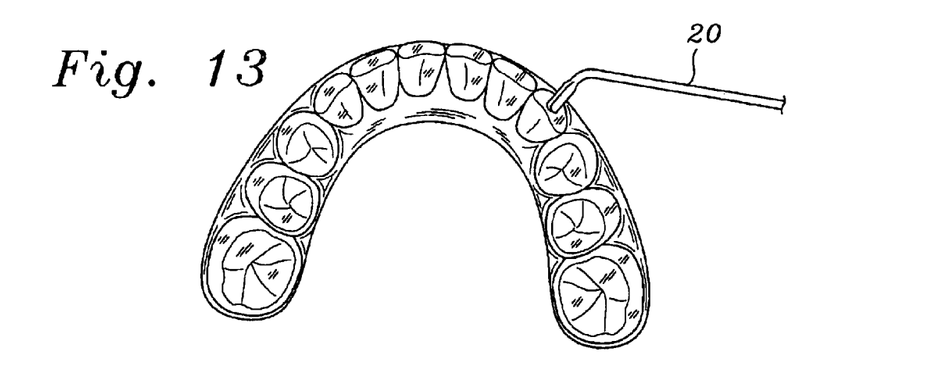
FIG. 13 is an occlusal view of the repositioner appliance as shown in FIG, 10 with an instrument retightening the stretched area.

The wire, as illustrated in FIG. 14, is most effectively embedded in the plate material when small bends 40 are placed in the wire. These bends are placed in a direction away from the surface of the model, allowing the plate material to lock under the wire. The wire 30, as shown in FIG. 14, also serves to stabilize the appliance and make it more retentive when worn by the patient. The stability and retentiveness enhances the effectiveness in moving the patient's teeth. Many other materials and forms of materials may be used to reinforce the appliance in the palatal area. Some materials may require a design pattern, as shown in FIG. 13, which produces a mechanical lock with the plate material. Other reinforcing materials, such as polymers and plastics, may be designed to produce a mechanical lock, or when the materials allow, they can be joined to the plate adhesively or by applying heat.

Figure 15:
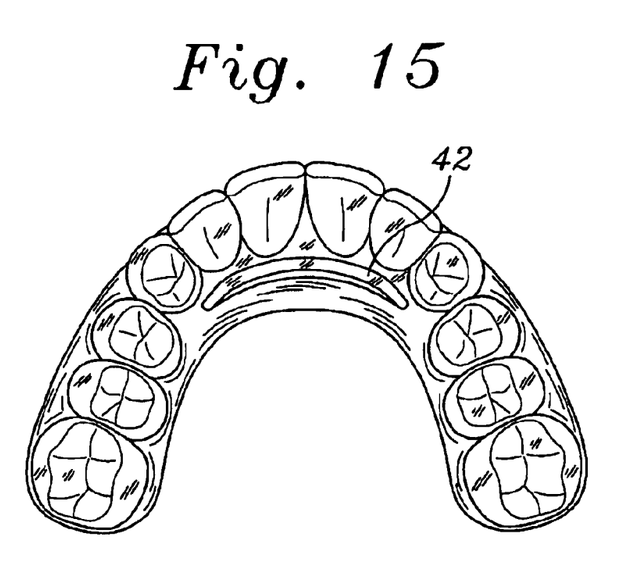
FIG. 15 is an occlusal view of another embodiment of the tooth repositioner.
Figure 16:
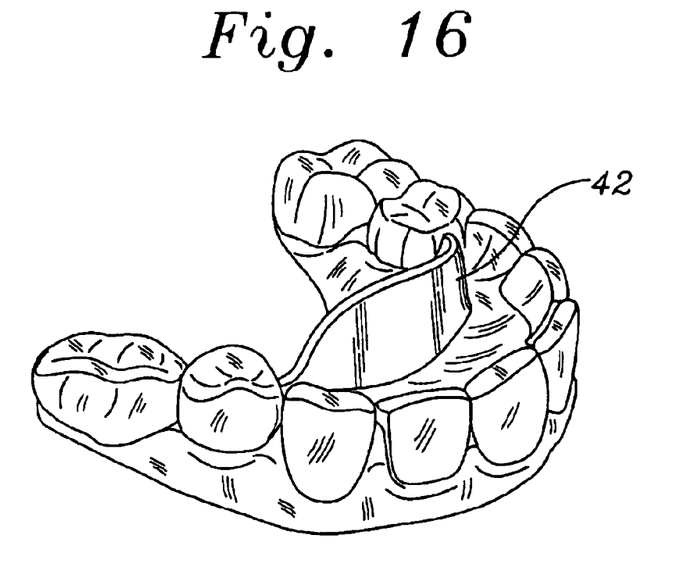
FIG. 16 is posterior view of the embodiment of the tooth repositioner of FIG. 15.
Figure 17:
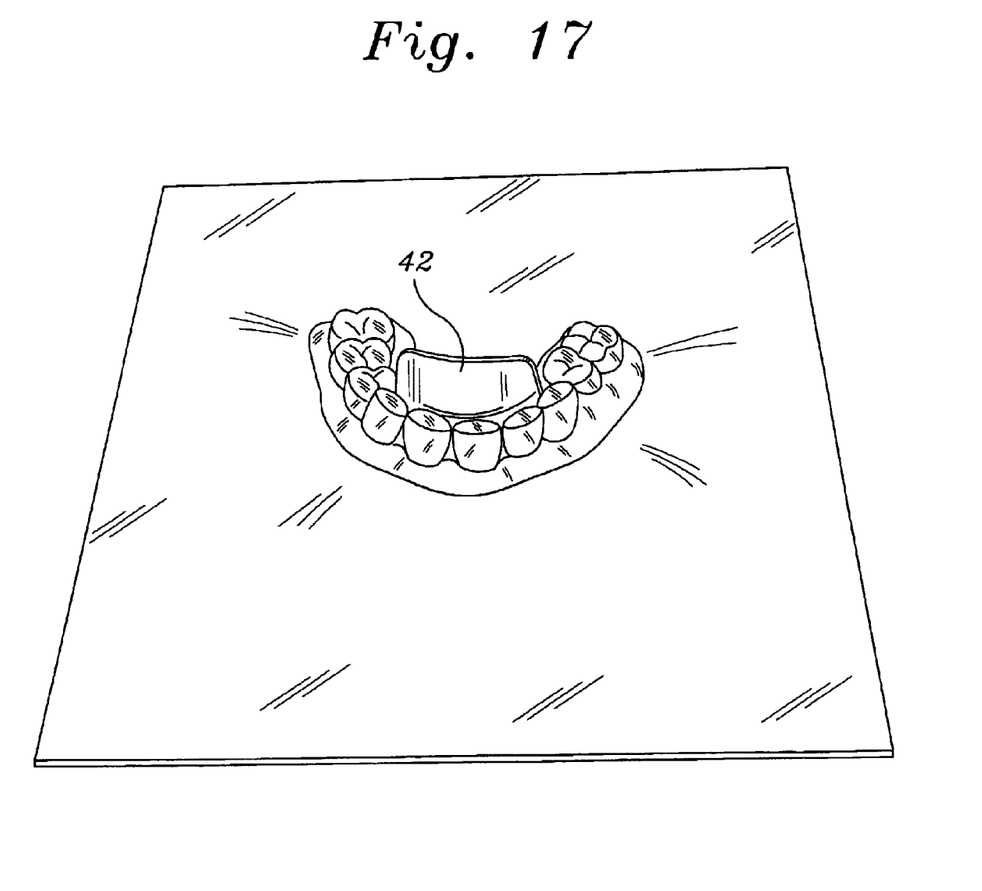
FIG. 17 is a side view of the embodiment of the tooth repositioner of FIGS. 15 and 16.
Figure 18:
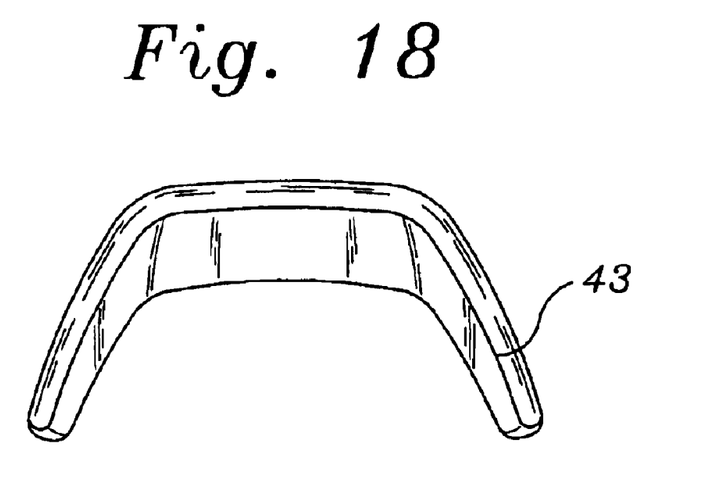
FIG. 18 is an occlusal view of the template for the tongue shield.
Figure 19:
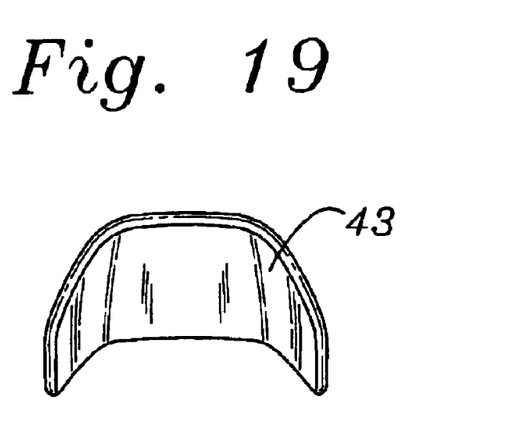
FIG. 19 is a posterior view of the template for the tongue shield of FIG. 18.

In another preferred embodiment a tongue habit shield 42, FIGS. 15 and 17 is an integral part of the appliance. Some patients place their tongue between their upper and lower anterior teeth, producing a dental open bite where their anterior teeth do not touch in occlusion. The shield 42 serves to keep the tongue away from this area, this is especially important following orthodontic treatment of a patient who had an open bite pretreatment. Orthodontists for many years have used a series of vertical wires, appropriately named a hay rake, to control the tongue's habit. The integral tongue shield is much easier to construct and much more comfortable for the patient to wear. In a preferred embodiment, the appliance is vacuum formed from 0.030 inch polypropylene, a template 43 FIG. 18 of the tongue shield 42 is formed using the 0.030 inch polypropylene material. The shield 42 is curved to follow the lingual curvature of the anterior teeth, extending from the cuspid area to the opposite side. The vertical height of the shield varies from patient to patient, but would extend, for an upper appliance, from the palatal surface vertically to the lingual-gingival area of the patient's lower teeth. To form the appliance, the shield 42 is placed in a vertical position on the model, as in FIGS. 15, 16, and 17, and the 0.030 in. polypropylene sheet is vacuum-formed over the shield template thereby forming a tongue appliance with the template as an integral part of the appliance.

The intent of the invention is to orthodontically move a patient's teeth effectively with a minimum number of appliances in an efficient and economic manner with an appliance which is simple and economic to construct. The orthodontic tooth repositioner is most useful for re-treatment of orthodontic relapses, particularly, where the posterior bite is correct in the anterior teeth have relapsed.

What is claimed:

1. A removable orthodontic repositioning appliance comprising:
    a vacuum-pressure thermo formed tooth portion of the appliance fitted to the posterior teeth;
    a vacuum-pressure thermo formed tooth portion fitted to the anterior teeth which have been aligned;
    a vacuum-pressure thermo formed labial gingival area portion fitted to the labial gingiva;
    a vacuum-pressure thermo formed lingual or palatal portion fitted to the palate of the maxilla and the lingual area of the mandible; and
    a lingually and palatally mounted arcuate wire with bends away from the lingual and palatal surfaces which enhance the embedding of the arcuate wire in the lingual and palatal thermo formed portion of the appliance.

2. An appliance as in claim 1 wherein the appliance is thermo formed from a 0.030 inch sheet of polypropylene.

3. An appliance as in claim 1 wherein the arcuate wire is 0.045 inch polypropylene.

4. A removable orthodontic repositioning appliance comprising:
    a vacuum-pressure thermo formed tooth portion fitted to the posterior teeth;
    a vacuum-pressure thermo formed tooth portion fitted to the anterior teeth which have been aligned;
    a vacuum-pressure thermo formed labial gingival area portion fitted to the labial gingival;
    a vacuum-pressure thermo formed lingual or palatal portion fitted to palate of the maxilla and the lingual area of the mandible; and
    a lingually and palatally mounted arcuate wire bends away from the lingual and palatal surfaces which enhances the embedding of the arcuate wire in the lingual and palatal thermo formed portion of the appliance; and
    an 8 mm section of the embedded wire adjacent to the incisors is open to the tissue side of the appliance to allow for the widening or narrowing adjustments of the wire.

5. A removable orthodontic repositioning appliance comprising:
    a removable appliance fitted to teeth wherein selected misaligned teeth, using a model of the teeth, are aligned to an ideal position by moving the teeth, adapting a sheet of material to the model, forming the appliance, and the patient wearing the appliance to align the teeth;
    a tongue habit shield integrated into the appliance wherein the shield is formed by placing a shield template lingual to the incisors and vacuum forming the appliance material over the model containing the shield whereby the removable appliance functions as a habit shield, preventing adverse effects of a patient's tongue upon their teeth; and
    a shield template formed from the appliance material formed in an arc to follow the lingual of the six anterior teeth and extending from the first bicuspid to first bicuspid and having sufficient height to extend to the gingival area of the opposing teeth when the patient has their teeth in closed position.

6. An appliance as in claim 5 wherein air holes are placed the shield area to facilitate the patient's breathing.

7. An appliance as in claim 5 wherein the tongue habit shield is placed palatal to the posterior teeth in order to prevent adverse lateral tongue pressure upon the posterior teeth.

8. An appliance as in claim 5 wherein the reinforcing material is 0.020 to 0.080 inch diameter wire in an arcuate form lingual to the teeth, extending from the molar areas to the incisors, wherein bends are placed in the wire which raise the wire away from the palatal tissue surface, enhancing mechanical retention of the wire to the appliance material, the bends the most effective when placed near the ends of the wire in the molar area.

9. A method for constructing and using an appliance for repositioning teeth comprising:
    arranging teeth on a dental model from a misaligned position to an aligned position;
    forming a 0.045" wire into an arcuate axis form with small bends upwardly from the surface of the model;
    placing the arcuate wire in the tooth model in the palate of the upper model and the lingual gingival area of the lower model;
    covering the anterior 8 mm of the arcuate wire with a putty;
    thermo forming a 0.030 inch sheet of polypropylene over the model with the arcuate wire, the polypropylene fully enclosing small bends of the arcuate wire, wherein the 8 mm portion of the arcuate wire is open to the palatal and lingual gingival area;
    seating the appliance in patients mouth;
    cutting the appliance from the incisal to the gingival area to loosen the appliance in the situation where the teeth are spaced;
    stretching the appliance material where if contacts the out of line teeth;
    retightening the appliance in the stretched area until the patient's teeth are aligned;
    widening the dental arch for by adjusting the arch of the arcuate wire in the open arcuate wire area; and
    narrowing the arch by adjusting the arcuate wire in the open arcuate wire area.

10. A method of making and using the appliance as in claim 9 further comprising:
    forming a tongue shield template from the polypropylene material in an arc similar to the lingual arch form of the upper anterior teeth;
    placing the tongue shield template vertically of the palate area of the upper model lingual to the upper incisors wherein the curvator follows the incisors; and
    thermo forming the 0.30" sheet of polypropylene over the model containing the arcuate wire wherein a tongue shield is formed preventing the tongue from adversely affecting the patient's anterior teeth when the appliance is worn.

* * * * *